United States Patent
Vlasov et al.

(10) Patent No.: US 9,260,482 B2
(45) Date of Patent: Feb. 16, 2016

(54) SYNTHETIC PEPTIDES WITH A NON-NARCOTIC TYPE OF ANALGESIC EFFECT

(71) Applicants: Oleg Arkadyevich Kotin, Gatchina (RU); Gennady Petrovich Vlasov, St. Petersburg (RU); Arkadiy Mihajlovich Kotin, St. Petersburg (RU)

(72) Inventors: Gennady Petrovich Vlasov, St. Petersburg (RU); Arkadiy Mihajlovich Kotin, St. Petersburg (RU)

( * ) Notice: Subject to any disclaimer, the term of this patent is extended or adjusted under 35 U.S.C. 154(b) by 0 days.

(21) Appl. No.: 14/386,675

(22) PCT Filed: Dec. 7, 2012

(86) PCT No.: PCT/RU2012/001036
§ 371 (c)(1),
(2) Date: Sep. 19, 2014

(87) PCT Pub. No.: WO2013/141750
PCT Pub. Date: Sep. 26, 2013

(65) Prior Publication Data
US 2015/0073123 A1     Mar. 12, 2015

(30) Foreign Application Priority Data
Mar. 22, 2012 (RU) ................. 2012110908

(51) Int. Cl.
*A61K 38/00* (2006.01)
*C07K 7/06* (2006.01)

(52) U.S. Cl.
CPC .. *C07K 7/06* (2013.01); *A61K 38/00* (2013.01)

(58) Field of Classification Search
CPC ................................. A61K 38/00; C07K 7/06
USPC ................................... 530/300, 329
See application file for complete search history.

(56) References Cited

PUBLICATIONS

N. A. Patkina i dr. Izuchenie analgeticheskoi aktivnosti fragmentov kaltsitonina, Khimiko-farmatsevticheskii zhurnal, 1994, vol. 28, N° 10, p. 31-34, skhema 1 na p. 32.
I.V. Rogachevskii et al. Sintez i prostranstvennoe stroenie peptidov H-Leu-His-Lys-Leu-Gln-Thr-NH2 i H-Ala-D-Ala-Lys-Leu-Ala-Thr-NH2. ZHurnal obshchei khimii, 2005, vol. 75.
International Search Report for PCT/RU2012/001036 filed Dec. 12, 2012.

*Primary Examiner* — Julie Ha
(74) *Attorney, Agent, or Firm* — Notaro, Michalos & Zaccaria P.C.

(57) ABSTRACT

Synthetic peptides which have non-narcotic type of analgesic action which may be used in medicine and pharmacology as anesthetic anodynes according to the general formula 1 [SEQ ID NO:1] H-XDL-XDL1-XDL2-L-Lys-L-Leu-XDL3-L-Thr-R2 (I) are disclosed.

1 Claim, No Drawings

SYNTHETIC PEPTIDES WITH A NON-NARCOTIC TYPE OF ANALGESIC EFFECT

CROSS-REFERENCE TO SEQUENCE LISTING

The sequence listing, filed Nov. 24, 2014 (filename: Sequence-ID-5.txt, create date: Nov. 24, 2014, size: 2000 bytes) is herein incorporated by reference in its entirety.

FIELD OF INVENTION

The invention relates to biochemistry, more particularly, to biologically active peptides having non-narcotic type of analgesic action which may find use in medicine and pharmacology as anesthetic anodynes.

BACKGROUND

Different anesthetic preparations which are divided into narcotic (morphine and congenial structures) and non-narcotic analgesics (derivatives of salicylic acid, pyrazolone, aniline etc.) in terms of their chemical nature and mode of action are known. All the above mentioned analgesics have certain disadvantages which sharply narrow down possibilities of their application in medicine (M. D. Mashkovsky. Medicinal products, Kharkov: "Torsing" publishing house, 1997, edition 13, pp. 144-145).

The known peptide analgesics are synthetic analogs of natural enkephalins and endorphins, such as opioid peptides (Casy A. F., Parfitt A. C., Opioid analgesics: Chemistry and receptors. New York, Plenum Press, 1986, 445-502; Lierz P., Stefan Punsmann S., 2008). Their main disadvantage is that anesthetic activity is accompanied by habituation and narcotic action. Moreover, narcotic analgesics are not effective in all pain syndromes (Fallon M. When morphine does not work. *Support Care Cancer.* 2008 Feb. 15).

Peptide analgesics which have non-narcotic type of anesthesia not causing habituation and narcotic action are also known. Their anesthetic action is developed through non-opioid receptors and neurotransmitters. Synthetic and, more recently, recombinant calcitonins, anesthetic action of which is implemented through specific calcitonin receptors and brain serotonergic system, have gained the most widespread currency in that group (Yasushi Kuraishi/Neuropeptide action of calcitonin-analgesic effect/ in Magazine Kidney and Metabolic Bone Disease, V. 14 No 03). The most commonly used is synthetic sequence corresponding to salmon calcitonin as the most active one among all known calcitonins. Salmon calcitonin is a polypeptide hormone consisting of 32 residues of amino acids with molecular weight of 3,454.93 Dalton. Its structure represents an alpha helix (Andreotti G. et al, 2006).

Salmon calcitonin has long-term anesthetic action and presently exists in different pharmaceutical forms: in the form of spray or drops for intranasal use, oral and intramuscular administration, as well as in the form of suppositories.

However full-length calcitonins have a variety of essential disadvantages, including:

1) Hormonal activity, impact on calcium and phosphoric metabolism. In this connection calcitonins may not be used during pregnancy and labor pain relief because of possibility of teratogenic and long-term effects for the offspring.

2) Immunologic activity. Therefore, during long-term use of calcitonin, as is the case in treatment and prevention of osteoporosis, neutralizing antibodies are formed, that reduces effectiveness of use of calcitonin (Levy F et al., Formation of Neutralizing Antibodies During Intranasal Synthetic Salmon Calcitonin Treatment of Pagets Disease. 1988, 67, 3, 541-545).

3) Full-length calcitonins contain amyloidogenic sequence Gly2-Gln14 which is common for many amyloidogenic proteins (Steven S.-S. Wang[1], Theresa A. Good[2] and Dawn L. Rymer[3]).

4) The cost of full-length calcitonin synthesis and treatment with this preparation is very high. For that reason calcitonins are referred to orphan drugs which are used only when there are no alternative ways of treatment, for example, in case of Paget's disease (Maresca V. Human calcitonin in the Management of osteoporosis: A multicenter Study.—J. Int. Med. Res., 1985, 13, 311-316).

For the purpose of elimination of the specified disadvantages we have separated a fragment of salmon calcitonin which comprises 16-21 amino acids of salmon calcitonin (hereinafter referred to as $CT_{16-21}$) called the "active centre" of calcitonin (G. P. Vlasov, V. R. Glushenkova, A. M. Kotin et al. (1989) "Search of Active Centre of Calcitonin", Chemistry of Peptides and Proteins 4, 89) (SEQ ID NO: 12):

```
16  17  18  19  20  21
Leu-His-Lys-Leu-Gln-Thr
```

It was shown that the natural fragment of salmon calcitonin, $CT_{16-21}$ peptide, has high analgesic activity in the rat formalin test which allows identifying non-narcotic type of anesthesia, whereas it does not have immunologic activity, impact on calcium metabolism and does not contain amyloidogenic sequence. Comparison with similar sequences (16-21) of human, swine, bovine and rat calcitonins revealed greater activity as opposed to the latter ones. (A. M. Kotin, G. P. Vlasov et al. (1988) "Search of "active centre" and comparative study of full-length calcitonin and sequence 16-21 of different calcitonins in various physiological tests. Abstracts of the "Peptide Physiology" symposium", Leningrad, 106).

DETAILED DESCRIPTION

The object of the present invention is extension of a range of effective drugs which have non-narcotic type of analgesic action and are obtained by simple synthesis.

The set objective is solved in that synthetic peptides of the general formula 1 [SEQ ID NO:1] are suggested:

$$H\text{-}XDL\text{-}XDL1\text{-}XDL2\text{-}L\text{-}Lys\text{-}L\text{-}Leu\text{-}XDL3\text{-}L\text{-}Thr\text{-}R2 \quad (I),$$

where:

H is hydrogen,

XDL is absence of amino acid or L-Tyr,

XDL1 is one of the following amino acids: L-Leu, L-Ala or D-Ala,

XDL2 is one of the following amino acids: L-His, D-His, L-Ala or D-Ala,

XDL3 is one of the following amino acids: L-Gln, L-Ala or D-Ala;

R2 is OMe or $NH_2$, or peptides—retro-inversions of the formula (I) which have reverse sequence of amino acids with replacement of L-form of amino acids with D-form and D-form of amino acids with L-form in the general formula 2 [SEQ ID NO:2]

$$H\text{-}D\text{-}Thr\text{-}XDL4\text{-}D\text{-}Leu\text{-}D\text{-}Lys\text{-}XDL5\text{-}XDL6\text{-}XDL7\text{-}R2 \quad (II),$$

where:

H is hydrogen,

XDL4 is one of the following amino acids: D-Gln, D-Ala or L-Ala;

XDL5 is one of the following amino acids: D-His, L-His, D-Ala or L-Ala,

XDL6 is one of the following amino acids: D-Leu, D-Ala or L-Ala,

XDL7 is absence of amino acid or D-Tyr,

R2 is OMe or $NH_2$, as anesthetic preparations with non-narcotic type of analgesic action.

The suggested peptides have anesthetic action, including upon systemic injection and intranasal administration.

The essence of the invention is that it was established by an experiment that the claimed peptides having the simple structure which simplifies their obtainment by chemical means possess high anesthetic activity verified by analgesic tests conducted on animals.

Some peptides of the general formula I, II are presented in the table 1:

TABLE 1

Some amino acid sequences for the claimed peptides corresponding to the general formula I or II.

SEQ ID NO: 1

| H- | L-Leu- | L-His- | L-Lys- | L-Leu- | L-Gln- | L-Thr- | OMe |
|---|---|---|---|---|---|---|---|
| H- | L-Leu- | L-His- | L-Lys- | L-Leu- | L-Gln- | L-Thr- | $NH_2$ |
| H- | L-Ala- | L-His- | L-Lys- | L-Leu- | L-Gln- | L-Thr- | OMe |
| H- | L-Ala- | L-His- | L-Lys- | L-Leu- | L-Gln- | L-Thr- | $NH_2$ |
| H- | D-Ala- | L-His- | L-Lys- | L-Leu- | L-Gln- | L-Thr- | OMe |
| H- | D-Ala- | L-His- | L-Lys- | L-Leu- | L-Gln- | L-Thr- | $NH_2$ |
| H- | L-Leu- | D-His- | L-Lys- | L-Leu- | L-Gln- | L-Thr- | OMe |
| H- | L-Leu- | D-His- | L-Lys- | L-Leu- | L-Gln- | L-Thr- | $NH_2$ |
| H- | L-Ala- | D-His- | L-Lys- | L-Leu- | L-Gln- | L-Thr- | OMe |
| H- | L-Ala- | D-His- | L-Lys- | L-Leu- | L-Gln- | L-Thr- | $NH_2$ |
| H- | D-Ala- | D-His- | L-Lys- | L-Leu- | L-Gln- | L-Thr- | OMe |
| H- | D-Ala- | D-His- | L-Lys- | L-Leu- | L-Gln- | L-Thr- | $NH_2$ |
| H- | L-Leu- | L-Ala- | L-Lys- | L-Leu- | L-Gln- | L-Thr- | OMe |
| H- | L-Leu- | L-Ala- | L-Lys- | L-Leu- | L-Gln- | L-Thr- | $NH_2$ |
| H- | L-Ala- | L-Ala- | L-Lys- | L-Leu- | L-Gln- | L-Thr- | OMe |
| H- | L-Ala- | L-Ala- | L-Lys- | L-Leu- | L-Gln- | L-Thr- | $NH_2$ |
| H- | D-Ala- | L-Ala- | L-Lys- | L-Leu- | L-Gln- | L-Thr- | OMe |
| H- | D-Ala- | L-Ala- | L-Lys- | L-Leu- | L-Gln- | L-Thr- | $NH_2$ |
| H- | L-Leu- | D-Ala- | L-Lys- | L-Leu- | L-Gln- | L-Thr- | OMe |
| H- | L-Leu- | D-Ala- | L-Lys- | L-Leu- | L-Gln- | L-Thr- | $NH_2$ |
| H- | L-Ala- | D-Ala- | L-Lys- | L-Leu- | L-Gln- | L-Thr- | OMe |
| H- | L-Ala- | D-Ala- | L-Lys- | L-Leu- | L-Gln- | L-Thr- | $NH_2$ |
| H- | D-Ala- | D-Ala- | L-Lys- | L-Leu- | L-Gln- | L-Thr- | OMe |
| H- | D-Ala- | D-Ala- | L-Lys- | L-Leu- | L-Gln- | L-Thr- | $NH_2$ |
| H- | L-Leu- | L-His- | L-Lys- | L-Leu- | L-Ala- | L-Thr- | OMe |
| H- | L-Leu- | L-His- | L-Lys- | L-Leu- | L-Ala- | L-Thr- | $NH_2$ |
| H- | L-Ala- | L-His- | L-Lys- | L-Leu- | L-Ala- | L-Thr- | OMe |
| H- | L-Ala- | L-His- | L-Lys- | L-Leu- | L-Ala- | L-Thr- | $NH_2$ |
| H- | D-Ala- | L-His- | L-Lys- | L-Leu- | L-Ala- | L-Thr- | OMe |
| H- | D-Ala- | L-His- | L-Lys- | L-Leu- | L-Ala- | L-Thr- | $NH_2$ |
| H- | L-Leu- | D-His- | L-Lys- | L-Leu- | L-Ala- | L-Thr- | OMe |
| H- | L-Leu- | D-His- | L-Lys- | L-Leu- | L-Ala- | L-Thr- | $NH_2$ |
| H- | L-Ala- | D-His- | L-Lys- | L-Leu- | L-Ala- | L-Thr- | OMe |
| H- | L-Ala- | D-His- | L-Lys- | L-Leu- | L-Ala- | L-Thr- | $NH_2$ |
| H- | D-Ala- | D-His- | L-Lys- | L-Leu- | L-Ala- | L-Thr- | OMe |
| H- | D-Ala- | D-His- | L-Lys- | L-Leu- | L-Ala- | L-Thr- | $NH_2$ |
| H- | L-Leu- | L-Ala- | L-Lys- | L-Leu- | L-Ala- | L-Thr- | OMe |
| H- | L-Leu- | L-Ala- | L-Lys- | L-Leu- | L-Ala- | L-Thr- | $NH_2$ |
| H- | L-Ala- | L-Ala- | L-Lys- | L-Leu- | L-Ala- | L-Thr- | OMe |
| H- | L-Ala- | L-Ala- | L-Lys- | L-Leu- | L-Ala- | L-Thr- | $NH_2$ |
| H- | D-Ala- | L-Ala- | L-Lys- | L-Leu- | L-Ala- | L-Thr- | OMe |
| H- | D-Ala- | L-Ala- | L-Lys- | L-Leu- | L-Ala- | L-Thr- | $NH_2$ |
| H- | L-Leu- | D-Ala- | L-Lys- | L-Leu- | L-Ala- | L-Thr- | OMe |
| H- | L-Leu- | D-Ala- | L-Lys- | L-Leu- | L-Ala- | L-Thr- | $NH_2$ |
| H- | L-Ala- | D-Ala- | L-Lys- | L-Leu- | L-Ala- | L-Thr- | OMe |
| H- | L-Ala- | D-Ala- | L-Lys- | L-Leu- | L-Ala- | L-Thr- | $NH_2$ |
| H- | D-Ala- | D-Ala- | L-Lys- | L-Leu- | L-Ala- | L-Thr- | OMe |
| H- | D-Ala- | D-Ala- | L-Lys- | L-Leu- | L-Ala- | L-Thr- | $NH_2$ |
| H- | L-Leu- | L-His- | L-Lys- | L-Leu- | D-Ala- | L-Thr- | OMe |
| H- | L-Leu- | L-His- | L-Lys- | L-Leu- | D-Ala- | L-Thr- | $NH_2$ |
| H- | L-Ala- | L-His- | L-Lys- | L-Leu- | D-Ala- | L-Thr- | OMe |
| H- | L-Ala- | L-His- | L-Lys- | L-Leu- | D-Ala- | L-Thr- | $NH_2$ |
| H- | D-Ala- | L-His- | L-Lys- | L-Leu- | D-Ala- | L-Thr- | OMe |
| H- | D-Ala- | L-His- | L-Lys- | L-Leu- | D-Ala- | L-Thr- | $NH_2$ |
| H- | L-Leu- | D-His- | L-Lys- | L-Leu- | D-Ala- | L-Thr- | OMe |
| H- | L-Leu- | D-His- | L-Lys- | L-Leu- | D-Ala- | L-Thr- | $NH_2$ |
| H- | L-Ala- | D-His- | L-Lys- | L-Leu- | D-Ala- | L-Thr- | OMe |
| H- | L-Ala- | D-His- | L-Lys- | L-Leu- | D-Ala- | L-Thr- | $NH_2$ |
| H- | D-Ala- | D-His- | L-Lys- | L-Leu- | D-Ala- | L-Thr- | OMe |
| H- | D-Ala- | D-His- | L-Lys- | L-Leu- | D-Ala- | L-Thr- | $NH_2$ |
| H- | L-Leu- | L-Ala- | L-Lys- | L-Leu- | D-Ala- | L-Thr- | OMe |
| H- | L-Leu- | L-Ala- | L-Lys- | L-Leu- | D-Ala- | L-Thr- | $NH_2$ |
| H- | L-Ala- | L-Ala- | L-Lys- | L-Leu- | D-Ala- | L-Thr- | OMe |

TABLE 1-continued

Some amino acid sequences for the claimed peptides corresponding to the general formula I or II.

| | | | | | | | | |
|---|---|---|---|---|---|---|---|---|
| H- | L-Ala- | L-Ala- | L-Lys- | L-Leu- | D-Ala- | L-Thr- | NH$_2$ | |
| H- | D-Ala- | L-Ala- | L-Lys- | L-Leu- | D-Ala- | L-Thr- | OMe | |
| H- | D-Ala- | L-Ala- | L-Lys- | L-Leu- | D-Ala- | L-Thr- | NH$_2$ | |
| H- | L-Leu- | D-Ala- | L-Lys- | L-Leu- | D-Ala- | L-Thr- | OMe | |
| H- | L-Leu- | D-Ala- | L-Lys- | L-Leu- | D-Ala- | L-Thr- | NH$_2$ | |
| H- | L-Ala- | D-Ala- | L-Lys- | L-Leu- | D-Ala- | L-Thr- | OMe | |
| H- | L-Ala- | D-Ala- | L-Lys- | L-Leu- | D-Ala- | L-Thr- | NH$_2$ | |
| H- | D-Ala- | D-Ala- | L-Lys- | L-Leu- | D-Ala- | L-Thr- | OMe | |
| H- | D-Ala- | D-Ala- | L-Lys- | L-Leu- | D-Ala- | L-Thr- | NH$_2$ | |
| H- | L-Tyr- | L-Leu- | L-His- | L-Lys- | L-Leu- | L-Gln- | L-Thr- | OMe |
| H- | L-Tyr- | L-Leu- | L-His- | L-Lys- | L-Leu- | L-Gln- | L-Thr- | NH$_2$ |
| H- | L-Tyr- | L-Ala- | L-His- | L-Lys- | L-Leu- | L-Gln- | L-Thr- | OMe |
| H- | L-Tyr- | L-Ala- | L-His- | L-Lys- | L-Leu- | L-Gln- | L-Thr- | NH$_2$ |
| H- | L-Tyr- | D-Ala- | L-His- | L-Lys- | L-Leu- | L-Gln- | L-Thr- | OMe |
| H- | L-Tyr- | D-Ala- | L-His- | L-Lys- | L-Leu- | L-Gln- | L-Thr- | NH$_2$ |
| H- | L-Tyr- | L-Leu- | D-His- | L-Lys- | L-Leu- | L-Gln- | L-Thr- | OMe |
| H- | L-Tyr- | L-Leu- | D-His- | L-Lys- | L-Leu- | L-Gln- | L-Thr- | NH$_2$ |
| H- | L-Tyr- | L-Ala- | D-His- | L-Lys- | L-Leu- | L-Gln- | L-Thr- | OMe |
| H- | L-Tyr- | L-Ala- | D-His- | L-Lys- | L-Leu- | L-Gln- | L-Thr- | NH$_2$ |
| H- | L-Tyr- | D-Ala- | D-His- | L-Lys- | L-Leu- | L-Gln- | L-Thr- | OMe |
| H- | L-Tyr- | D-Ala- | D-His- | L-Lys- | L-Leu- | L-Gln- | L-Thr- | NH$_2$ |
| H- | L-Tyr- | L-Leu- | L-Ala- | L-Lys- | L-Leu- | L-Gln- | L-Thr- | OMe |
| H- | L-Tyr- | L-Leu- | L-Ala- | L-Lys- | L-Leu- | L-Gln- | L-Thr- | NH$_2$ |
| H- | L-Tyr- | L-Ala- | L-Ala- | L-Lys- | L-Leu- | L-Gln- | L-Thr- | OMe |
| H- | L-Tyr- | L-Ala- | L-Ala- | L-Lys- | L-Leu- | L-Gln- | L-Thr- | NH$_2$ |
| H- | L-Tyr- | D-Ala- | L-Ala- | L-Lys- | L-Leu- | L-Gln- | L-Thr- | OMe |
| H- | L-Tyr- | D-Ala- | L-Ala- | L-Lys- | L-Leu- | L-Gln- | L-Thr- | NH$_2$ |
| H- | L-Tyr- | L-Leu- | D-Ala- | L-Lys- | L-Leu- | L-Gln- | L-Thr- | OMe |
| H- | L-Tyr- | L-Leu- | D-Ala- | L-Lys- | L-Leu- | L-Gln- | L-Thr- | NH$_2$ |
| H- | L-Tyr- | L-Ala- | D-Ala- | L-Lys- | L-Leu- | L-Gln- | L-Thr- | OMe |
| H- | L-Tyr- | L-Ala- | D-Ala- | L-Lys- | L-Leu- | L-Gln- | L-Thr- | NH$_2$ |
| H- | L-Tyr- | D-Ala- | D-Ala- | L-Lys- | L-Leu- | L-Gln- | L-Thr- | OMe |
| H- | L-Tyr- | D-Ala- | D-Ala- | L-Lys- | L-Leu- | L-Gln- | L-Thr- | NH$_2$ |
| H- | L-Tyr- | L-Leu- | L-His- | L-Lys- | L-Leu- | L-Ala- | L-Thr- | OMe |
| H- | L-Tyr- | L-Leu- | L-His- | L-Lys- | L-Leu- | L-Ala- | L-Thr- | NH$_2$ |
| H- | L-Tyr- | L-Ala- | L-His- | L-Lys- | L-Leu- | L-Ala- | L-Thr- | OMe |
| H- | L-Tyr- | L-Ala- | L-His- | L-Lys- | L-Leu- | L-Ala- | L-Thr- | NH$_2$ |
| H- | L-Tyr- | D-Ala- | L-His- | L-Lys- | L-Leu- | L-Ala- | L-Thr- | OMe |
| H- | L-Tyr- | D-Ala- | L-His- | L-Lys- | L-Leu- | L-Ala- | L-Thr- | NH$_2$ |
| H- | L-Tyr- | L-Leu- | D-His- | L-Lys- | L-Leu- | L-Ala- | L-Thr- | OMe |
| H- | L-Tyr- | L-Leu- | D-His- | L-Lys- | L-Leu- | L-Ala- | L-Thr- | NH$_2$ |
| H- | L-Tyr- | L-Ala- | D-His- | L-Lys- | L-Leu- | L-Ala- | L-Thr- | OMe |
| H- | L-Tyr- | L-Ala- | D-His- | L-Lys- | L-Leu- | L-Ala- | L-Thr- | NH$_2$ |
| H- | L-Tyr- | D-Ala- | D-His- | L-Lys- | L-Lcu- | L-Ala- | L-Thr- | OMe |
| H- | L-Tyr- | D-Ala- | D-His- | L-Lys- | L-Leu- | L-Ala- | L-Thr- | NH$_2$ |
| H- | L-Tyr- | L-Leu- | L-Ala- | L-Lys- | L-Leu- | L-Ala- | L-Thr- | OMe |
| H- | L-Tyr- | L-Leu- | L-Ala- | L-Lys- | L-Leu- | L-Ala- | L-Thr- | NH$_2$ |
| H- | L-Tyr- | L-Ala- | L-Ala- | L-Lys- | L-Leu- | L-Ala- | L-Thr- | OMe |
| H- | L-Tyr- | L-Ala- | L-Ala- | L-Lys- | L-Leu- | L-Ala- | L-Thr- | NH$_2$ |
| H- | L-Tyr- | D-Ala- | L-Ala- | L-Lys- | L-Leu- | L-Ala- | L-Thr- | OMe |
| H- | L-Tyr- | D-Ala- | L-Ala- | L-Lys- | L-Leu- | L-Ala- | L-Thr- | NH$_2$ |
| H- | L-Tyr- | L-Leu- | D-Ala- | L-Lys- | L-Leu- | L-Ala- | L-Thr- | OMe |
| H- | L-Tyr- | L-Leu- | D-Ala- | L-Lys- | L-Leu- | L-Ala- | L-Thr- | NH$_2$ |
| H- | L-Tyr- | L-Ala- | D-Ala- | L-Lys- | L-Leu- | L-Ala- | L-Thr- | OMe |
| H- | L-Tyr- | L-Ala- | D-Ala- | L-Lys- | L-Leu- | L-Ala- | L-Thr- | NH$_2$ |
| H- | L-Tyr- | D-Ala- | D-Ala- | L-Lys- | L-Leu- | L-Ala- | L-Thr- | OMe |
| H- | L-Tyr- | D-Ala- | D-Ala- | L-Lys- | L-Leu- | L-Ala- | L-Thr- | NH$_2$ |
| H- | L-Tyr- | L-Leu- | L-His- | L-Lys- | L-Leu- | D-Ala- | L-Thr- | OMe |
| H- | L-Tyr- | L-Leu- | L-His- | L-Lys- | L-Leu- | D-Ala- | L-Thr- | NH$_2$ |
| H- | L-Tyr- | L-Ala- | L-His- | L-Lys- | L-Leu- | D-Ala- | L-Thr- | OMe |
| H- | L-Tyr- | L-Ala- | L-His- | L-Lys- | L-Leu- | D-Ala- | L-Thr- | NH$_2$ |
| H- | L-Tyr- | D-Ala- | L-His- | L-Lys- | L-Leu- | D-Ala- | L-Thr- | OMe |
| H- | L-Tyr- | D-Ala- | L-His- | L-Lys- | L-Leu- | D-Ala- | L-Thr- | NH$_2$ |
| H- | L-Tyr- | L-Leu- | D-His- | L-Lys- | L-Leu- | D-Ala- | L-Thr- | OMe |
| H- | L-Tyr- | L-Leu- | D-His- | L-Lys- | L-Leu- | D-Ala- | L-Thr- | NH2 |
| H- | L-Tyr- | L-Ala- | D-His- | L-Lys- | L-Leu- | D-Ala- | L-Thr- | OMe |
| H- | L-Tyr- | L-Ala- | D-His- | L-Lys- | L-Leu- | D-Ala- | L-Thr- | NH$_2$ |
| H- | L-Tyr- | D-Ala- | D-His- | L-Lys- | L-Leu- | D-Ala- | L-Thr- | OMe |
| H- | L-Tyr- | D-Ala- | D-His- | L-Lys- | L-Leu- | D-Ala- | L-Thr- | NH$_2$ |
| H- | L-Tyr- | L-Leu- | L-Ala- | L-Lys- | L-Leu- | D-Ala- | L-Thr- | OMe |
| H- | L-Tyr- | L-Leu- | L-Ala- | L-Lys- | L-Leu- | D-Ala- | L-Thr- | NH$_2$ |
| H- | L-Tyr- | L-Ala- | L-Ala- | L-Lys- | L-Leu- | D-Ala- | L-Thr- | OMe |
| H- | L-Tyr- | L-Ala- | L-Ala- | L-Lys- | L-Leu- | D-Ala- | L-Thr- | NH$_2$ |
| H- | L-Tyr- | D-Ala- | L-Ala- | L-Lys- | L-Leu- | D-Ala- | L-Thr- | OMe |
| H- | L-Tyr- | D-Ala- | L-Ala- | L-Lys- | L-Leu- | D-Ala- | L-Thr- | NH$_2$ |
| H- | L-Tyr- | L-Leu- | D-Ala- | L-Lys- | L-Leu- | D-Ala- | L-Thr- | OMe |
| H- | L-Tyr- | L-Leu- | D-Ala- | L-Lys- | L-Leu- | D-Ala- | L-Thr- | NH$_2$ |

TABLE 1-continued

Some amino acid sequences for the claimed peptides corresponding to the general formula I or II.

| H- | L-Tyr- | L-Ala- | D-Ala- | L-Lys- | L-Leu- | D-Ala- | L-Thr- | OMe |
| --- | --- | --- | --- | --- | --- | --- | --- | --- |
| H- | L-Tyr- | L-Ala- | D-Ala- | L-Lys- | L-Leu- | D-Ala- | L-Thr- | $NH_2$ |
| H- | L-Tyr- | D-Ala- | D-Ala- | L-Lys- | L-Leu- | D-Ala- | L-Thr- | OMe |
| H- | L-Tyr- | D-Ala- | D-Ala- | L-Lys- | L-Leu- | D-Ala- | L-Thr- | $NH_2$ |

SEQ ID NO: 2

| H- | D-Thr- | D-Gln- | D-Leu- | D-Lys- | D-His- | D-Leu- | OMe |
| --- | --- | --- | --- | --- | --- | --- | --- |
| H- | D-Thr- | D-Gln- | D-Leu- | D-Lys- | D-His- | D-Leu- | $NH_2$ |
| H- | D-Thr- | D-Gln- | D-Leu- | D-Lys- | D-His- | D-Ala- | OMe |
| H- | D-Thr- | D-Gln- | D-Leu- | D-Lys- | D-His- | D-Ala- | $NH_2$ |
| H- | D-Thr- | D-Gln- | D-Leu- | D-Lys- | D-His- | L-Ala- | OMe |
| H- | D-Thr- | D-Gln- | D-Leu- | D-Lys- | D-His- | L-Ala- | $NH_2$ |
| H- | D-Thr- | D-Gln- | D-Leu- | D-Lys- | L-His- | D-Leu- | OMe |
| H- | D-Thr- | D-Gln- | D-Leu- | D-Lys- | L-His- | D-Leu- | $NH_2$ |
| H- | D-Thr- | D-Gln- | D-Leu- | D-Lys- | L-His- | D-Ala- | OMe |
| H- | D-Thr- | D-Gln- | D-Leu- | D-Lys- | L-His- | D-Ala- | $NH_2$ |
| H- | D-Thr- | D-Gln- | D-Leu- | D-Lys- | L-His- | L-Ala- | OMe |
| H- | D-Thr- | D-Gln- | D-Leu- | D-Lys- | L-His- | L-Ala- | $NH_2$ |
| H- | D-Thr- | D-Gln- | D-Leu- | D-Lys- | D-Ala- | D-Leu- | OMe |
| H- | D-Thr- | D-Gln- | D-Leu- | D-Lys- | D-Ala- | D-Leu- | $NH_2$ |
| H- | D-Thr- | D-Gln- | D-Leu- | D-Lys- | D-Ala- | D-Ala- | OMe |
| H- | D-Thr- | D-Gln- | D-Leu- | D-Lys- | D-Ala- | D-Ala- | $NH_2$ |
| H- | D-Thr- | D-Gln- | D-Leu- | D-Lys- | D-Ala- | L-Ala- | OMe |
| H- | D-Thr- | D-Gln- | D-Leu- | D-Lys- | D-Ala- | L-Ala- | $NH_2$ |
| H- | D-Thr- | D-Gln- | D-Leu- | D-Lys- | L-Ala- | D-Leu- | OMe |
| H- | D-Thr- | D-Gln- | D-Leu- | D-Lys- | L-Ala- | D-Leu- | $NH_2$ |
| H- | D-Thr- | D-Gln- | D-Leu- | D-Lys- | L-Ala- | D-Ala- | OMe |
| H- | D-Thr- | D-Gln- | D-Leu- | D-Lys- | L-Ala- | D-Ala- | $NH_2$ |
| H- | D-Thr- | D-Gln- | D-Leu- | D-Lys- | L-Ala- | L-Ala- | OMe |
| H- | D-Thr- | D-Gln- | D-Leu- | D-Lys- | L-Ala- | L-Ala- | $NH_2$ |
| H- | D-Thr- | D-Ala- | D-Leu- | D-Lys- | D-His- | D-Leu- | OMe |
| H- | D-Thr- | D-Ala- | D-Leu- | D-Lys- | D-His- | D-Leu- | $NH_2$ |
| H- | D-Thr- | D-Ala- | D-Leu- | D-Lys- | D-His- | D-Ala- | OMe |
| H- | D-Thr- | D-Ala- | D-Leu- | D-Lys- | D-His- | D-Ala- | $NH_2$ |
| H- | D-Thr- | D-Ala- | D-Leu- | D-Lys- | D-His- | L-Ala- | OMe |
| H- | D-Thr- | D-Ala- | D-Leu- | D-Lys- | D-His- | L-Ala- | $NH_2$ |
| H- | D-Thr- | D-Ala- | D-Leu- | D-Lys- | L-His- | D-Leu- | OMe |
| H- | D-Thr- | D-Ala- | D-Leu- | D-Lys- | L-His- | D-Leu- | $NH_2$ |
| H- | D-Thr- | D-Ala- | D-Leu- | D-Lys- | L-His- | D-Ala- | OMe |
| H- | D-Thr- | D-Ala- | D-Leu- | D-Lys- | L-His- | D-Ala- | $NH_2$ |
| H- | D-Thr- | D-Ala- | D-Leu- | D-Lys- | L-His- | L-Ala- | OMe |
| H- | D-Thr- | D-Ala- | D-Leu- | D-Lys- | L-His- | L-Ala- | $NH_2$ |
| H- | D-Thr- | D-Ala- | D-Leu- | D-Lys- | D-Ala- | D-Leu- | OMe |
| H- | D-Thr- | D-Ala- | D-Leu- | D-Lys- | D-Ala- | D-Leu- | $NH_2$ |
| H- | D-Thr- | D-Ala- | D-Leu- | D-Lys- | D-Ala- | D-Ala- | OMe |
| H- | D-Thr- | D-Ala- | D-Leu- | D-Lys- | D-Ala- | D-Ala- | $NH_2$ |
| H- | D-Thr- | D-Ala- | D-Leu- | D-Lys- | D-Ala- | L-Ala- | OMe |
| H- | D-Thr- | D-Ala- | D-Leu- | D-Lys- | D-Ala- | L-Ala- | $NH_2$ |
| H- | D-Thr- | D-Ala- | D-Leu- | D-Lys- | L-Ala- | D-Leu- | OMe |
| H- | D-Thr- | D-Ala- | D-Leu- | D-Lys- | L-Ala- | D-Leu- | $NH_2$ |
| H- | D-Thr- | D-Ala- | D-Leu- | D-Lys- | L-Ala- | D-Ala- | OMe |
| H- | D-Thr- | D-Ala- | D-Leu- | D-Lys- | L-Ala- | D-Ala- | $NH_2$ |
| H- | D-Thr- | D-Ala- | D-Leu- | D-Lys- | L-Ala- | L-Ala- | OMe |
| H- | D-Thr- | D-Ala- | D-Leu- | D-Lys- | L-Ala- | L-Ala- | $NH_2$ |
| H- | D-Thr- | L-Ala- | D-Leu- | D-Lys- | D-His- | D-Leu- | OMe |
| H- | D-Thr- | L-Ala- | D-Leu- | D-Lys- | D-His- | D-Leu- | $NH_2$ |
| H- | D-Thr- | L-Ala- | D-Leu- | D-Lys- | D-His- | D-Ala- | OMe |
| H- | D-Thr- | L-Ala- | D-Leu- | D-Lys- | D-His- | D-Ala- | $NH_2$ |
| H- | D-Thr- | L-Ala- | D-Leu- | D-Lys- | D-His- | L-Ala- | OMe |
| H- | D-Thr- | L-Ala- | D-Leu- | D-Lys- | D-His- | L-Ala- | $NH_2$ |
| H- | D-Thr- | L-Ala- | D-Leu- | D-Lys- | L-His- | D-Leu- | OMe |
| H- | D-Thr- | L-Ala- | D-Leu- | D-Lys- | L-His- | D-Leu- | $NH_2$ |
| H- | D-Thr- | L-Ala- | D-Leu- | D-Lys- | L-His- | D-Ala- | OMe |
| H- | D-Thr- | L-Ala- | D-Leu- | D-Lys- | L-His- | D-Ala- | $NH_2$ |
| H- | D-Thr- | L-Ala- | D-Leu- | D-Lys- | L-His- | L-Ala- | OMe |
| H- | D-Thr- | L-Ala- | D-Leu- | D-Lys- | L-His- | L-Ala- | $NH_2$ |
| H- | D-Thr- | L-Ala- | D-Leu- | D-Lys- | D-Ala- | D-Leu- | OMe |
| H- | D-Thr- | L-Ala- | D-Leu- | D-Lys- | D-Ala- | D-Leu- | $NH_2$ |
| H- | D-Thr- | L-Ala- | D-Leu- | D-Lys- | D-Ala- | D-Ala- | OMe |
| H- | D-Thr- | L-Ala- | D-Leu- | D-Lys- | D-Ala- | D-Ala- | $NH_2$ |
| H- | D-Thr- | L-Ala- | D-Leu- | D-Lys- | D-Ala- | L-Ala- | OMe |
| H- | D-Thr- | L-Ala- | D-Leu- | D-Lys- | D-Ala- | L-Ala- | $NH_2$ |
| H- | D-Thr- | L-Ala- | D-Leu- | D-Lys- | L-Ala- | D-Leu- | OMe |
| H- | D-Thr- | L-Ala- | D-Leu- | D-Lys- | L-Ala- | D-Leu- | $NH_2$ |
| H- | D-Thr- | L-Ala- | D-Leu- | D-Lys- | L-Ala- | D-Ala- | OMe |
| H- | D-Thr- | L-Ala- | D-Leu- | D-Lys- | L-Ala- | D-Ala- | $NH_2$ |

TABLE 1-continued

Some amino acid sequences for the claimed peptides
corresponding to the general formula I or II.

| | | | | | | | |
|---|---|---|---|---|---|---|---|
| H- | D-Thr- | L-Ala- | D-Leu- | D-Lys- | L-Ala- | L-Ala- | OMe |
| H- | D-Thr- | L-Ala- | D-Leu- | D-Lys- | L-Ala- | L-Ala- | NH$_2$ |
| H- | D-Thr- | D-Gln- | D-Leu- | D-Lys- | D-His- | D-Leu- | D-Tyr- OMe |
| H- | D-Thr- | D-Gln- | D-Leu- | D-Lys- | D-His- | D-Leu- | D-Tyr- NH$_2$ |
| H- | D-Thr- | D-Gln- | D-Leu- | D-Lys- | D-His- | D-Ala- | D-Tyr- OMe |
| H- | D-Thr- | D-Gln- | D-Leu- | D-Lys- | D-His- | D-Ala- | D-Tyr- NH$_2$ |
| H- | D-Thr- | D-Gln- | D-Leu- | D-Lys- | D-His- | L-Ala- | D-Tyr- OMe |
| H- | D-Thr- | D-Gln- | D-Leu- | D-Lys- | D-His- | L-Ala- | D-Tyr- NH$_2$ |
| H- | D-Thr- | D-Gln- | D-Leu- | D-Lys- | L-His- | D-Leu- | D-Tyr- OMe |
| H- | D-Thr- | D-Gln- | D-Leu- | D-Lys- | L-His- | D-Leu- | D-Tyr- NH$_2$ |
| H- | D-Thr- | D-Gln- | D-Leu- | D-Lys- | L-His- | D-Ala- | D-Tyr- OMe |
| H- | D-Thr- | D-Gln- | D-Leu- | D-Lys- | L-His- | D-Ala- | D-Tyr- NH$_2$ |
| H- | D-Thr- | D-Gln- | D-Leu- | D-Lys- | L-His- | L-Ala- | D-Tyr- OMe |
| H- | D-Thr- | D-Gln- | D-Leu- | D-Lys- | L-His- | L-Ala- | D-Tyr- NH$_2$ |
| H- | D-Thr- | D-Gln- | D-Leu- | D-Lys- | D-Ala- | D-Leu- | D-Tyr- OMe |
| H- | D-Thr- | D-Gln- | D-Leu- | D-Lys- | D-Ala- | D-Leu- | D-Tyr- NH$_2$ |
| H- | D-Thr- | D-Gln- | D-Leu- | D-Lys- | D-Ala- | D-Ala- | D-Tyr- OMe |
| H- | D-Thr- | D-Gln- | D-Leu- | D-Lys- | D-Ala- | D-Ala- | D-Tyr- NH$_2$ |
| H- | D-Thr- | D-Gln- | D-Leu- | D-Lys- | D-Ala- | L-Ala- | D-Tyr- OMe |
| H- | D-Thr- | D-Gln- | D-Leu- | D-Lys- | D-Ala- | L-Ala- | D-Tyr- NH$_2$ |
| H- | D-Thr- | D-Gln- | D-Leu- | D-Lys- | L-Ala- | D-Leu- | D-Tyr- OMe |
| H- | D-Thr- | D-Gln- | D-Leu- | D-Lys- | L-Ala- | D-Leu- | D-Tyr- NH$_2$ |
| H- | D-Thr- | D-Gln- | D-Leu- | D-Lys- | L-Ala- | D-Ala- | D-Tyr- OMe |
| H- | D-Thr- | D-Gln- | D-Leu- | D-Lys- | L-Ala- | D-Ala- | D-Tyr- NH$_2$ |
| H- | D-Thr- | D-Gln- | D-Leu- | D-Lys- | L-Ala- | L-Ala- | D-Tyr- OMe |
| H- | D-Thr- | D-Gln- | D-Leu- | D-Lys- | L-Ala- | L-Ala- | D-Tyr- NH$_2$ |
| H- | D-Thr- | D-Ala- | D-Leu- | D-Lys- | D-His- | D-Leu- | D-Tyr- OMe |
| H- | D-Thr- | D-Ala- | Ü-Leu- | D-Lys- | D-His- | D-Leu- | D-Tyr- NH$_2$ |
| H- | D-Thr- | D-Ala- | D-Leu- | D-Lys- | D-His- | D-Ala- | D-Tyr- OMe |
| H- | D-Thr- | D-Ala- | D-Leu- | D-Lys- | D-His- | D-Ala- | D-Tyr- NH$_2$ |
| H- | D-Thr- | D-Ala- | D-Leu- | D-Lys- | D-His- | L-Ala- | D-Tyr- OMe |
| H- | D-Thr- | D-Ala- | D-Leu- | D-Lys- | D-His- | L-Ala- | D-Tyr- NH$_2$ |
| H- | D-Thr- | D-Ala- | D-Leu- | D-Lys- | L-His- | D-Leu- | D-Tyr- OMe |
| H- | D-Thr- | D-Ala- | D-Leu- | D-Lys- | L-His- | D-Leu- | D-Tyr- NH$_2$ |
| H- | D-Thr- | D-Ala- | D-Leu- | D-Lys- | L-His- | D-Ala- | D-Tyr- OMe |
| H- | D-Thr- | D-Ala- | D-Leu- | D-Lys- | L-His- | D-Ala- | D-Tyr- NH$_2$ |
| H- | D-Thr- | D-Ala- | D-Leu- | D-Lys- | L-His- | L-Ala- | D-Tyr- OMe |
| H- | D-Thr- | D-Ala- | D-Leu- | D-Lys- | L-His- | L-Ala- | D-Tyr- NH$_2$ |
| H- | D-Thr- | D-Ala- | D-Leu- | D-Lys- | D-Ala- | D-Leu- | D-Tyr- OMe |
| H- | D-Thr- | D-Ala- | D-Leu- | D-Lys- | D-Ala- | D-Leu- | D-Tyr- NH$_2$ |
| H- | D-Thr- | D-Ala- | D-Leu- | D-Lys- | D-Ala- | D-Ala- | D-Tyr- OMe |
| H- | D-Thr- | D-Ala- | D-Leu- | D-Lys- | D-Ala- | D-Ala- | D-Tyr- NH$_2$ |
| H- | D-Thr- | D-Ala- | D-Leu- | D-Lys- | D-Ala- | L-Ala- | D-Tyr- OMe |
| H- | D-Thr- | D-Ala- | D-Leu- | D-Lys- | D-Ala- | L-Ala- | D-Tyr- nH$_2$ |
| H- | D-Thr- | D-Ala- | D-Leu- | D-Lys- | L-Ala- | D-Leu- | D-Tyr- OMe |
| H- | D-Thr- | D-Ala- | D-Leu- | D-Lys- | L-Ala- | D-Leu- | D-Tyr- NH$_2$ |
| H- | D-Thr- | D-Ala- | D-Leu- | D-Lys- | L-Ala- | D-Ala- | D-Tyr- OMe |
| H- | D-Thr- | D-Ala- | D-Leu- | D-Lys- | L-Ala- | D-Ala- | D-Tyr- NH$_2$ |
| H- | D-Thr- | D-Ala- | D-Leu- | D-Lys- | L-Ala- | L-Ala- | D-Tyr- OMe |
| H- | D-Thr- | D-Ala- | D-Leu- | D-Lys- | L-Ala- | L-Ala- | D-Tyr- NH$_2$ |
| H- | D-Thr- | L-Ala- | D-Leu- | D-Lys- | D-His- | D-Leu- | D-Tyr- OMe |
| H- | D-Thr- | L-Ala- | D-Leu- | D-Lys- | D-His- | D-Leu- | D-Tyr- NH$_2$ |
| H- | D-Thr- | L-Ala- | D-Leu- | D-Lys- | D-His- | D-Ala- | D-Tyr- OMe |
| H- | D-Thr- | L-Ala- | D-Leu- | D-Lys- | D-His- | D-Ala- | D-Tyr- NH$_2$ |
| H- | D-Thr- | L-Ala- | D-Leu- | D-Lys- | D-His- | L-Ala- | D-Tyr- OMe |
| H- | D-Thr- | L-Ala- | D-Leu- | D-Lys- | D-His- | L-Ala- | D-Tyr- NH$_2$ |
| H- | D-Thr- | L-Ala- | D-Leu- | D-Lys- | L-His- | D-Leu- | D-Tyr- OMe |
| H- | D-Thr- | L-Ala- | D-Leu- | D-Lys- | L-His- | D-Leu- | D-Tyr- NH$_2$ |
| H- | D-Thr- | L-Ala- | D-Leu- | D-Lys- | L-His- | D-Ala- | D-Tyr- OMe |
| H- | D-Thr- | L-Ala- | D-Leu- | D-Lys- | L-His- | D-Ala- | D-Tyr- NH$_2$ |
| H- | D-Thr- | L-Ala- | D-Leu- | D-Lys- | L-His- | L-Ala- | D-Tyr- OMe |
| H- | D-Thr- | L-Ala- | D-Leu- | D-Lys- | L-His- | L-Ala- | D-Tyr- NH$_2$ |
| H- | D-Thr- | L-Ala- | D-Leu- | D-Lys- | D-Ala- | D-Leu- | D-Tyr- OMe |
| H- | D-Thr- | L-Ala- | D-Leu- | D-Lys- | D-Ala- | D-Leu- | D-Tyr- NH$_2$ |
| H- | D-Thr- | L-Ala- | D-Leu- | D-Lys- | D-Ala- | D-Ala- | D-Tyr- OMe |
| H- | D-Thr- | L-Ala- | D-Leu- | D-Lys- | D-Ala- | D-Ala- | D-Tyr- NH$_2$ |
| H- | D-Thr- | L-Ala- | D-Leu- | D-Lys- | D-Ala- | L-Ala- | D-Tyr- OMe |
| H- | D-Thr- | L-Ala- | D-Leu- | D-Lys- | D-Ala- | L-Ala- | D-Tyr- NH$_2$ |
| H- | D-Thr- | L-Ala- | D-Leu- | D-Lys- | L-Ala- | D-Leu- | D-Tyr- OMe |
| H- | D-Thr- | L-Ala- | D-Leu- | D-Lys- | L-Ala- | D-Leu- | D-Tyr- nH$_2$ |
| H- | D-Thr- | L-Ala- | D-Leu- | D-Lys- | L-Ala- | D-Ala- | D-Tyr- OMe |
| H- | D-Thr- | L-Ala- | D-Leu- | D-Lys- | L-Ala- | D-Ala- | D-Tyr- NH$_2$ |

TABLE 1-continued

Some amino acid sequences for the claimed peptides
corresponding to the general formula I or II.

| H- | D-Thr- | L-Ala- | D-Leu- | D-Lys- | L-Ala- | L-Ala- | D-Tyr- | OMe |
| H- | D-Thr- | L-Ala- | D-Leu- | D-Lys- | L-Ala- | L-Ala- | D-Tyr- | $NH_2$ |

All peptides of this family had analgesic activity.

EMBODIMENTS OF INVENTION

Synthesis of peptides of the formula I was conducted by methods of peptide chemistry, solid-phase synthesis method with use of L- or D-amino acids.

Example 1

Synthesis of Peptide
H-Leu-His-Lys-Leu-Gln-Thr-Tyr-$NH_2$

The peptide H-Leu-His-Lys-Leu-Gln-Thr-Tyr-NH2 was obtained by method of automatic solid-phase synthesis according to the Fmoc scheme on Rink resin (Rink Amide Resin, 0.6 mmol of amino groups per 1 g of resin) with use of DCC/HOBt (N,N'-dicyclohexylcarbodiimide/1-hydroxybenzotriazol) amino acid activation method.

Releasing was conducted by way of treatment with piperidine/DMF (piperidine/K,K-dimethyl formamide) solution (1:4) for 7 minutes. Protection of groups of side chains was conducted with the following groups: tBu (tert-butyl ether) for tyrosine and threonine, Trt (trityl or triphenylmethyl) for glutamine and histidine, Boc (t-butyloxycarbonyl) for lysine. Peptides were cleaved from resin and released with the TFA/$H_2O$/EDT mixture (trifluoroacetic acid/water/1,2-ethandithiol) (90:5:5). Clearance of peptides was conducted by way of reversed-phase HPLC (C18 column), eluent-acetonitrile-water (0.1M of potassium dihydrogen phosphate) in the proportion of 6:4. Peptides were characterized with the help of a mass spectrometer.

Replacement of amino acids was performed in certain positions of the $CT_{16-21}$ peptide, and it was revealed how it affects anesthetic properties of obtained peptides. Analgesic activity of newly synthesized peptides was examined in the "formalin test" which allows discovering non-narcotic type of anesthesia (Wheeler-Aceto H., Porrea F., A. Cowan. The rat paw formalin test: comparison of noxious agents. Pain, 40 (1990), 229-238).

Example 2

Examination of Analgesic Activity of Newly Synthesized Peptides

Analgesic activity of newly synthesized peptides was examined as follows. Rats weighing 180-200 g were suboccipitally injected with the study peptide under ether anesthesia using a microdispenser in 10 µl of normal saline. Control animals were similarly injected with the equal amount of normal saline. After 20 minutes, 50 mcl of formalin solution at a dilution of 1:50 was injected into the dorsal surface of the right hind paw. The time of peptide injection and formalin dilution has been developed earlier. Each rat was used only once. The most clear behavioral indicators of pain reaction were expressed in paw tucking, licking, nibbling and jolting. Moreover, the first acute reaction to pain lasting for 6-7 min in control animals was followed by the dormant period: a rat lowered its paw, grooming behavior and nibbling was stopped. Then the reaction was repeated with expression not less than the previous one—it was the second phase of pain reaction.

The moment of paw tucking (beginning of the 1st phase of pain reaction), duration of this reaction, duration of dormancy and time of onset of the second phase of reaction—repeated paw tucking or its absence—were visually recorded in order to obtain quantitative data. Peptide was injected 20 min prior to formalin injection in case of suboccipital method of peptide injection and 30 min prior to formalin injection in case of intranasal method.

I. "L-alanine scanning" was performed when natural amino acids in different positions of the $CT_{16-21}$ peptide were successively replaced with "simple" L-alanine amino acid, and it was investigated how this affects peptide analgesic activity. Activity of 10 synthetic peptides synthesized in accordance with the Example 1 was compared both with the control (normal saline) and $CT_{16-21}$ as per technique described in the Example 2. Results are given in tables 2 and 3, where Ala-16, Ala-17, Ala-18 etc. are peptides similar to $CT_{16-21}$, wherein alanine is in the corresponding position.

TABLE 2

Analgesic actitivy of peptides when replacing amino acids in different positions with L-alanine (rats, suboccipital injection).

| PEPTIDE | Dose µg/rat | Number of rats | Time of pain reaction onset (sec) | Duration of the first peak of pain reaction (sec) |
|---|---|---|---|---|
| Control | — | 62* | 6 (2) | 435 (13) |
| $CT_{16-21}$ | 0.001 | 10 | 17 (6) | 394 (34) |
| $CT_{16-21}$ | 0.01 | 11 | 19 (8) | 328 (21) |
| $CT_{16-21}$ | 0.1 | 22 | 39 (8) a < 0.001 | 263 (20) a < 0.001 |
| Ala-16 | 0.001 | 18 | 10 (2) | 426 (28) |
| Ala-16 | 0.01 | 9 | 38 (11) a < 0.01 | 323 (42) a < 0, 02 |
| Ala-16 | 0.1 | 9 | 52 (14) a < 0.002 | 299 (39) a < 0.002 |
| Ala-17 | 0.001 | 8 | 6 (4) | 388 (40) |
| Ala-17 | 0.01 | 14 | 60 (17) a < 0.05 | 282 (43) a < 0.05 |
| Ala-17 | 0.1 | 10 | 70 (20) a < 0.002 | 300 (21) a < 0.002 |
| Ala-18 | 0.1 | 9 | 39 (15) a < 0.1 | 374 (32) a < 0.1 |
| Ala-19 | 0.1 | 14 | 25 (10) a < 0.1 | 294 (26) a < 0.1 |
| Ala-20 | 0.001 | 13 | 12 (4) a < 0.1 | 378 (26) a < 0.1 |
| Ala-20 | 0.01 | 8 | 46 (13) a < 0.1 | 338 (56) a < 0.1) |
| Ala-20 | 0.1 | 9 | 43 (18) a < 0 < 001 | 206 (43) a < 0.001 |
| Ala-21 | 0.1 | 7 | 7 (2) | 272 (27) a < 0.02 |

TABLE 3

Comparasion of analgesic activity of peptides at the dose of 1 µg per rat

| Peptide | Number of rats | Beginning of pain reaction | Duration of the 1st peak (sec) | Beginning of the 2nd peak (min) | Number of animals which do not have the 2nd peak of reaction |
|---|---|---|---|---|---|
| Control | 62* | 5 ± 2 | 435 ± 13 | 18 ± 3 | 1 |
| $CT_{16-21}$ | 28 | 30 ± 6 | 284 ± 20 | 21 ± 2 | 4 |

TABLE 3-continued

Comparasion of analgesic activity of peptides at the dose of 1 μg per rat

| Peptide | Number of rats | Beginning of pain reaction | Duration of the 1st peak (sec) | Beginning of the 2nd peak (min) | Number of animals which do not have the 2nd peak of reaction |
|---|---|---|---|---|---|
| L-Ala-16 | 10 | 80 ± 22<br>a < 0.001 | 264 ± 41<br>a < 0.001 | 21 ± 2<br>(n = 24) | 1 |
| L-Ala-17 | 9 | 75 ± 15<br>a < 0.002 | 217 ± 21<br>a < 0.001 | 21 ± 4<br>(n = 9) | 3 |
| L-Ala-18 | 9 | 44 ± 18<br>a < 0.001 | 274 ± 46<br>a < 0.001 | 19 ± 2<br>(n = 6) | 4 |
| L-Ala-19 | 10 | 13 ± 5<br>a < 0.05 | 330 ± 38<br>a < 0.002 | 18 ± 2<br>(n = 5) | 3 |
| L-Ala-20 | 10 | 56 ± 20<br>a < 0.05 | 226 ± 31<br>a < 0.02 | 16 ± 20<br>(n = 7) | 3 |
| L-Ala-21 | 12 | 24 ± 9<br>a < 0.02 | 265 ± 26<br>a < 0.001 | 16 ± 2<br>(n = 7) | 1 |
|  |  | a < 0.05 | a < 0.001 | (n = 11) |  |

As can be seen in tables 2, 3 replacement of amino acids in positions 18 and particularly 19 and 21 with L-alanine is accompanied by certain peptide activity drop. Beginning of pain reaction at the dose as low as 0.1 μg per rat does not differ from the control one reliably. However, duration of pain reaction was less than in control rats at the dose of 1 μg upon replacement with L-alanine in the position 19 and at the dose of 0.1 μg in case of replacements in peptide positions 19 and 20. Furthermore, it appeared that prevention of the second peak of pain reaction is observed in equal proportions both in initial peptide and in case of replacements with alanine in positions 18, 19 and 21. This points to nonequivalence of mechanisms of the first and second peaks of pain reaction and impact of amino acid replacement in peptide thereon.

On the contrary, replacement of amino acid in positions 16, 17 and 20 with L-alanine did not have an essential impact on peptide analgesic activity, and in some cases (for example, when replacing histidine with alanine in the position 17) activity was even higher to some extent both according to the criterion of onset delay of pain reaction as well as its duration criterion. This shows possibility of replacement of the "complex" and expensive histidine amino acid with the "simple" and cheap alanine without activity loss. The tendency of increase of relative number of animals which do not have the second reaction peak in case of replacement of natural amino acids with L-alanine in positions 17 and 20 was revealed as well.

Main conclusions which can be drawn from the data presented in tables 2 and 3 are as follows:

1. Replacement of amino acids in positions 18, 19 and 21 of salmon calcitonin with L-alanine leads to essential activity loss of initial peptide.

2. Replacement of amino acids in positions 16, 17 and 20 with L-alanine does not essentially affect initial peptide activity.

3. The clear tendency of peptide activity increase is observed in case of replacement of histidine with alanine in the fragment position 17.

II. "D-alanine scanning" was also performed when natural amino acids in different positions of the $CT_{16-21}$ peptide were successively replaced with "simple" D-alanine amino acid, and it was investigated how it affects peptide analgesic activity. Activity of synthetic peptides synthesized in accordance with the Example 1 having D-alanine replacement in the corresponding position was compared both with the control (normal saline) and $CT_{16-21}$ as per technique in the Example 2. Results are given in the table 4.

TABLE 4

Analgesic activity of peptides when replacing amino acids in different positions with D-alanine.

| Peptide | Number of rats | Beginning of pain reaction (sec) | Duration of the 1st peak of pain reaction | Beginning of the 2nd peak (min) | Number of rats which do not have the 2nd peak |
|---|---|---|---|---|---|
| Control | 13 | 4 (2) | 417 (15) | 11 (2) | — |
| 16-D-Ala 1 μg | 10 | 52 (9)<br>a < 0.001 | 333 (15)<br>a < 0.002 | 16 (2) | 2 |
| 17-D-Ala 16,20-L-Ala 1 μg | 16 | 40 (7)<br>a < 0.001 | 217 (15)<br>a < 0.001 | 18 (2) | 2 |
| 17-D-Ala 16,20-L-Ala 0.1 μg | 8 | 11 (4)<br>a < 0.1 | 300 (30)<br>a < 0.01 | 13 (1) | — |
| 18-D-Ala 1 μg | 9 | 32 (8)<br>a < 0.01 | 380 (15)<br>a < 0.002 | 15 (2) | 2 |
| 19-D-Ala 1 μg | 7 | 68 (17)<br>a < 0.002 | 337 (46)<br>a < 0.01 | 24 (2)<br>a < 0.001 | 4 |
| 20 D-Ala 1 μg | 10 | 27 (6)<br>a < 0.002 | 268 (27)<br>a < 0.001 | 15 (2)<br>a < 0.01 | — |
| 21 D-Ala 1 μg | 11 | 27 (7)<br>a < 0.01 | 345 (34)<br>a < 0.1 | 15 (2)<br>a = 0.02 | 1—no pain reaction |
| CGRP 1 μg | 5 | 5 (2) | 402 (36) | 17 (2) | — |

Analyzing the data presented in the table 4, it may be noted that replacement of amino acids in $CT_{16-21}$ with D-alanine did not lead to increase of analgesic activity as opposed to activity of initial $CT_{16-21}$. In this respect, analgesic activity is preserved to some extent in all variants of replacement. However, this reaction is highly specific, because, for example, a fragment of calcitonin gene related peptide (CGRP) does not have analgesic activity in this test at all. Replacement of methyl ether of the fragment 16-21 with dimethyl hydrazide derivative also deprives the $CT_{16-21}$ peptide fragment of the possibility to produce anesthetic action.

The highest degree of reliability of differences from the control of all three parameters characterizing analgesic action was observed during replacements of amino acid in the position 17 with D-Ala, and amino acids in positions 16 and 20 with L-Ala. In this variant, several animals did not have the second peak of reaction, though activity did not reach values observed in case of replacement of natural amino acid in the position 17 with D-histidine. Nevertheless, the latter one is a more expensive form of analgesic peptide. Main conclusions which can be drawn from the data presented in the table 4 are as follows:

4. Replacement of natural amino acids in $CT_{16-21}$ with D-alanine does not lead to essential activity change as opposed to natural sequence.

5. Peptide with replacements in the position 17 with D-Ala and in positions 16 and 20 with L-Ala is the most active compound.

III. There was established a possibility of increase of obtained peptides stability (duration of action) by way of replacement of natural L-amino acid with corresponding D-amino acid in order to reduce the rate of potential enzymic cleavage of peptide. Activity of synthetic peptides synthesized in accordance with the Example 1 was compared both with the control (normal saline) and natural peptide fragment $CT_{16-21}$ as per technique described in the Example 2. Results are given in the table 5.

TABLE 5

Analgesic activity of peptides with replacement of L-amino acids with corresponding D-amino acids in different positions corresponding with its number.

| Peptide | Number of rats | Beginning of pain reaction (sec) | Duration of the 1st peal of pain reaction | Beginning of the 2nd peak (min) | Number of rats which do not have the 2nd peak |
|---|---|---|---|---|---|
| Control (normal saline) | 22 | 6 (2) | 484 (17) | 17 (8) | — |
| 16 D-Leu 1 μg | 7 | 3 (1) | 449 (24) 1—none 1—paralyzed | 17 (2) | |
| 17-D-His 1 μg | 15 | 56 (17) $a < 0.01$ | 296 (41) $a < 0.001$ | 18 (2) $n = 8$ | 7 |
| 17-D-His 0.1 μg | 7 | 48 (14) $a < 0.001$ | 236 (21) $a < 0.001$ | | 7 |
| 18-D-Lys 1 μg | 10 | 91 (30) $a < 0.001$ | 303 (25) $a < 0.001$ | 18 (2) | 1 |
| 19-D-Leu 1 μg | | 327 (33) $a < 0.001$ | | 21 (2) | 1 |
| 20-D-Gln 1 μg | 9 | 20 (16) | 372 (23) $a < 0.001$ | 18 (2) | |

Based on the data presented in the table 5 it can be seen that the major differences from analgesic activity of the $CT_{16-21}$ control peptide are achieved in case of replacement of natural amino acid L-histidine in the position 17 with D-histidine: in this case almost a half of animals do not have the second peak of pain reaction and, which is very important, such a response is preserved when reducing the dose by 10 times. The shortest duration of the first peak of pain reaction was observed in the same case.

Among unfavorable replacements one should note replacement of L-leucine with D-leucine in the position 16 which led to undesirable side reaction—paralysis of one animal.

Main conclusions which can be drawn from the data presented in the table 5 are as follows:

6. Replacement of natural L-amino acids in $CT_{16-21}$ with corresponding D-amino acids did not lead to essential activity increase, except for replacement of L-histidine with D-histidine in the position 17. In this case, activity has increased substantially, whereas a half of animals did not have the second peak of pain reaction.

IV. Possibility of stability increase of 10 obtained peptides by way of modification of peptide terminal sequence was also established. Activity of synthetic peptides synthesized in accordance with the Example 1 was compared both with the control (normal saline) and $CT_{16-21}$ as per technique described in the Example 2. Results are given in the table 6.

TABLE 6

Assessment of analgesic activity of peptides modified with methyl ether or hydrazide in terminal amino acid.

| | | | | | | | % of rats | |
|---|---|---|---|---|---|---|---|---|
| No. | Peptides | Dose (μg) | Number of rats | Onset delay of pain reaction (sec) | Decrease in duration of the 1st phase | Without the 1st phase of pain reaction | Without the 2nd phase |
|---|---|---|---|---|---|---|---|
| 1 | $CT_{16-21H}$ | 1 | 10 | 91 ± 12 $\alpha < 0.01$ | 158 ± 26 $\alpha < 0.001$ | | 25 |
| | | 0.1 | 8 | 72 ± 14 $\alpha < 0.05$ | 110 ± 12 $\alpha < 0.01$ | | |
| | | 0.01 | 4 | 20 ± 8 | 20 ± 4 | | |
| 2 | $CT_{16-21H}$ | 10 | 11 | 19 ± 3 $\alpha < 0.01$ | 143 ± 21 $\alpha < 0.01$ | | |
| | | 1 | 13 | 17 ± 3 $\alpha < 0.01$ | 153 ± 12 $\alpha < 0.01$ | | |
| | | 0.1 | 14 | 7 ± 2 $\alpha < 0.05$ | 145 ± 12 $\alpha < 0.01$ | | 14 |
| | | 0.01 | 10 | 4 ± 3 | 110 ± 17 | | |
| 3 | $CT_{16-21OMe}$ | 10 | 16 | 27 ± 11 $\alpha < 0.01$ | 167 ± 25 $\alpha < 0.001$ | 18 | 25 |
| | | 1 | 35 | 22 ± 5 $\alpha < 0.01$ | 163 ± 20 $\alpha < 0.001$ | 5 | 48 |
| | | 0.1 | 21 | 21 ± 8 $\alpha < 0.01$ | 167 ± 15 $\alpha < 0.001$ | 33 | 10 |
| | | 0.01 | 19 | 14 ± 4 $\alpha < 0.1$ | 150 ± 20 $\alpha < 0.01$ | | |
| 4 | $CT_{16-21NH2}$ | 10 | 10 | 87 ± 23 $\alpha < 0.01$ | 185 ± 18 $\alpha < 0.001$ | | 14 |
| | | 1 | 19 | 91 ± 13 $\alpha < 0.02$ | 208 ± 28 $\alpha < 0.001$ | 26 | 42 |
| | | 0.1 | 8 | 60 ± 9 $\alpha < 0.01$ | 182 ± 23 $\alpha < 0.001$ | 12 | 33 |
| | | 0.001 | 6 | 25 ± 8 | 37 ± 12 | 17 | |

Pursuant to the provided data, the sequences (peptides) terminally modified with methyl ether and specifically hydrazide were the most active ones.

Main conclusions which can be drawn from the data presented in the table 5 are as follows:

6. Increase of stability of peptides without loss of their activity is possible by way of terminal modification with methyl ether or hydrazide.

V. Peptides—retro-inversions of the formula I corresponding to the formula II which have reverse sequence of amino acids with replacement of L-forms of amino acids with D-forms and D-forms of amino acids with L-forms were also investigated. Such peptides are distinguished by high resistance to all kinds of peptidases (Mariotti et al., European Patent EP0393786). Particularly, sequences D-Thr-D-Glu-D-Leu-D-Lys-D-His-D-Leu-NH$_2$ (retro-inversion $CT_{16-21}$) and D-Thr-D-Glu-D-Leu-D-15 Lys-L-His-D-Leu-NH2 (retro-inversion $CT_{16-21}$ with replacement of L-histidine in the position 17 with D-histidine) were investigated. Activity of synthetic peptides synthesized in accordance with the Example 1 was compared both with the control (normal saline) and $CT_{16-21}$ as per technique described in the Example 2. Results are given in the table 7.

Main conclusions which can be drawn from the data presented in the table 7 are as follows:

7. Peptides—retro-inversions of the formula (II) which have reverse sequence of amino acids with replacement of L-forms of amino acids with D-forms and D-forms of amino acids with L-forms possess high analgesic activity.

VI. Peptides with addition of L-Tyr amino acid sequence absent in the natural fragment of calcitonin on N-terminal were synthesized in the same way as described in the Example 1. Activity of synthesized synthetic peptides was compared both with the control (normal saline) and $CT_{16-21}$ as per technique described in the Example 2. Results are given in the table 8.

TABLE 7

Analgesic activity of $CT_{16-21}$ sequence with replacement of L-histidine in the position 17 with D-histidine, retro-inversion of this sequence and retro-inversion of $CT_{16-21}$ in case of intranasal administration method in citrate phosphate buffer. Peptide was injected 30 min prior to subcutaneous injection of formalin 2%.

| No. | Experiment | Number of rats | Dose (µg) | Beginning of pain reaction (sec) | Duration of the 1st peak of pain reaction | Beginning of the 2nd peak (min) |
|---|---|---|---|---|---|---|
| 1 | Control (citrate phosphate buffer) | 6 | | 8 ± 1 | 341 ± 23 | 15.5 ± 1.5 |
| 2 | 17 D-His | 7 | 10 | 35 ± 10 $\alpha < 0.05$ | 228 ± 13 $\alpha < 0.002$ | 21.2 ± 1.1 $\alpha < 0.02$ |
|   |   | 5 | 1 | 44 ± 37 | 410 ± 54 | two ones do not have the 2nd peak 20.5 3.5 |
| 3 | Complete retro-inversion $CT_{16-21}$ | 4 | 10 | 20 ± 9 | 333 ± 9 | 14.4 ± 1.0 |
|   |   | 5 | 1 | 12 ± 6 | 300 ± 46 | 17.4 ± 2.9 |
|   |   | 6 | 0.1 | 126 | 249 ± 20 $\alpha < 0.02$ | 16.2 ± 2.6 |
| 4 | 17 L-His- upon complete retro-inversion of $CT_{16-21}$ | 5 | 10 | 8 ± 3 | 314 ± 32 | 15.0 ± 1.6 |
|   |   | 6 | 1 | 10 ± 2 | 342 ± 26 | 12.5 ± 1.6, the first one has none |
|   |   | 3 | 0.1 | 48 ± 18 $\alpha < 0.1$ | 300 ± 10 | 21.0 ± 5.3 |

Pursuant to the provided data, it is possible to use peptides—retro-inversions of the formula (I) for analgesia.

TABLE 8

Analgesic activity of Tyr-16-21OMe sequence.

| Experiment | Dose µg | Number of rats | Onset delay of pain reaction | Decrease in duration of the first peak of pain reaction | % of animals without pain reaction | % of animals without the second peak of pain reaction |
|---|---|---|---|---|---|---|
| Tyr-16-21OMe | 10 | 4 | 27 ± 10 | 155 ± 35 $\alpha < 0.001$ | | 100 |
|   | 1 | 11 | 30 ± 15 | 134 ± 50 $\alpha < 0.05$ | | 60 |

Pursuant to the provided data, obtained peptides are effective in prevention of the second peak of pain reaction.

INDUSTRIAL APPLICABILITY

Thus, the examples given above prove possibility of producing of the suggested peptides which have high analgesic activity. Moreover, peptides with addition of L-Tyr amino acid sequence absent in the natural fragment of calcitonin on N-terminal are more effective in prevention of the second peak of pain reaction.

The technical result of the present invention is high analgesic activity and resistance of suggested peptides which allows considering them as the basis for creation of safe medicinal analgesic drugs with non-narcotic type of analgesic action.

What is claimed is:

1. Synthetic peptides of the general formula 1 [SEQ ID NO: 1]

$$H\text{-}XDL\text{-}XDL1\text{-}XDL2\text{-}L\text{-}Lys\text{-}L\text{-}Leu\text{-}XDL3\text{-}L\text{-}Thr\text{-}R2 \quad (1),$$

where:

H is hydrogen,

XDL is absence of amino acid or L-Tyr,

XDL1 is one of the following amino acids: L-Leu, L-Ala, or D-Ala,

XDL2 is one of the following amino acids: D-His, L-Ala or D-ALA,

XDL3 is L-Gln;

R2 is OMe or $NH_2$, as anesthetic preparations with non-narcotic type of analgesic action.

\* \* \* \* \*

SEQUENCE LISTING

```
<160> NUMBER OF SEQ ID NOS: 12

<210> SEQ ID NO 1
<211> LENGTH: 6
<212> TYPE: PRT
<213> ORGANISM: Artificial Sequence
<220> FEATURE:
<223> OTHER INFORMATION: Synthesized sequence

<400> SEQUENCE: 1

Ala His Lys Leu Gln Thr

<210> SEQ ID NO 2
<211> LENGTH: 6
<212> TYPE: PRT
<213> ORGANISM: Artificial Sequence
<220> FEATURE:
<223> OTHER INFORMATION: Synthesized sequence

<400> SEQUENCE: 2

Leu Ala Lys Leu Gln Thr

<210> SEQ ID NO 3
<211> LENGTH: 6
<212> TYPE: PRT
<213> ORGANISM: Artificial Sequence
<220> FEATURE:
<223> OTHER INFORMATION: Synthesized sequence

<400> SEQUENCE: 3

Ala Ala Lys Leu Gln Thr

<210> SEQ ID NO 4
<211> LENGTH: 6
<212> TYPE: PRT
<213> ORGANISM: Artificial Sequence
<220> FEATURE:
<223> OTHER INFORMATION: Synthesized sequence

<400> SEQUENCE: 4

Leu Ala Lys Leu Ala Thr

<210> SEQ ID NO 5
<211> LENGTH: 6
<212> TYPE: PRT
<213> ORGANISM: Artificial Sequence
<220> FEATURE:
<223> OTHER INFORMATION: Synthesized sequence

<400> SEQUENCE: 5

Ala Ala Lys Leu Ala Thr

<210> SEQ ID NO 6
<211> LENGTH: 7
<212> TYPE: PRT
<213> ORGANISM: Artificial Sequence
<220> FEATURE:
```

```
<223> OTHER INFORMATION: Synthesized sequence

<400> SEQUENCE: 6

Tyr Leu His Lys Leu Gln Thr

<210> SEQ ID NO 7
<211> LENGTH: 7
<212> TYPE: PRT
<213> ORGANISM: Artificial Sequence
<220> FEATURE:
<223> OTHER INFORMATION: Synthesized sequence

<400> SEQUENCE: 7

Tyr Leu Ala Lys Leu Gln Thr

<210> SEQ ID NO 8
<211> LENGTH: 7
<212> TYPE: PRT
<213> ORGANISM: Artificial Sequence
<220> FEATURE:
<223> OTHER INFORMATION: Synthesized sequence

<400> SEQUENCE: 8

Tyr Ala Ala Lys Leu Gln Thr

<210> SEQ ID NO 9
<211> LENGTH: 7
<212> TYPE: PRT
<213> ORGANISM: Artificial Sequence
<220> FEATURE:
<223> OTHER INFORMATION: Synthesized sequence

<400> SEQUENCE: 9

Tyr Leu His Lys Leu Ala Thr

<210> SEQ ID NO 10
<211> LENGTH: 7
<212> TYPE: PRT
<213> ORGANISM: Artificial Sequence
<220> FEATURE:
<223> OTHER INFORMATION: Synthesized sequence

<400> SEQUENCE: 10

Tyr Ala His Lys Leu Ala Thr

<210> SEQ ID NO 11
<211> LENGTH: 7
<212> TYPE: PRT
<213> ORGANISM: Artificial Sequence
<220> FEATURE:
<223> OTHER INFORMATION: Synthesized sequence

<400> SEQUENCE: 11

Tyr Leu Ala Lys Leu Ala Thr

<210> SEQ ID NO 12
<211> LENGTH: 6
<212> TYPE: PRT
<213> ORGANISM: Artificial Sequence
<220> FEATURE:
<223> OTHER INFORMATION: Synthesized sequence

<400> SEQUENCE: 12

Leu His Lys Leu Gln Thr
```